US00PP31845P2

(12) United States Plant Patent
Egger

(10) Patent No.: US PP31,845 P2
(45) Date of Patent: Jun. 2, 2020

(54) ***HEUCHERA* PLANT NAMED 'DARK 'N' BRIGHT'**

(50) Latin Name: ***Heuchera* hybrid**
Varietal Denomination: Dark 'N' Bright

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/501,734

(22) Filed: May 28, 2019

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 6/80
See application file for complete search history.

*Primary Examiner* — Anne Marie Grunberg
(74) *Attorney, Agent, or Firm* — Klarquist Sparkman, LLP

(57) ABSTRACT

A new and distinct *Heuchera* plant characterized by semi-matte, black to dark purple colored leaves, medium size, rounded lobes and lightly ruffled leaves, small, bi-colored flowers of hot pink and white on medium short spikes, good sun tolerance, a medium, low mounding habit with excellent crown count, and excellent vigor.

1 Drawing Sheet

Botanical denomination: *Heuchera* hybrid.

Variety designation: 'Dark 'N' Bright'.

Trademark designation: SIRENS' SONG™ 'Dark 'N' Bright'.

Cross reference to *Heuchera* 'Dark Night', applied for concurrently having application Ser. No. 16/501,733.

Cross reference to *Heuchera* 'Orange Delight', applied for concurrently having application Ser. No. 16/501,732.

BACKGROUND OF THE INVENTION

The present invention relates to a new and distinct cultivar of *Heuchera* given the cultivar name of 'Dark 'N' Bright'. *Heuchera* is in the family Saxifragaceae. *Heuchera* 'Dark 'N' Bright' originated as a controlled cross using *Heuchera* 'B122-9', a proprietary, unpatented, unnamed plant as the seed parent, and *Heuchera* 'B110-5', a proprietary plant as the pollen parent. These parents are a result of breeding plan to produce purple leaf *Heuchera* with good crowns.

Compared to the seed parent, *Heuchera* 'B122-9', the new cultivar has bi-color flowers of pink and white rather than solid hot pink flowers.

Compared to the pollen parent, *Heuchera* 'B110-5', the new cultivar has semi-matte leaves instead of shiny, shorter flower peduncles, and more crowns.

Compared to *Heuchera* 'Obsidian', U.S. Plant Pat. No. 14,836, the new cultivar has flowers that are bi-colored hot pink and white rather than yellow green.

Compared to *Heuchera* 'TNHEUNEB', U.S. Plant Pat. No. 30,583, the new cultivar is smaller in size, has brighter pink flowers and shorter peduncles, and is more free flowering.

This new *Heuchera* is uniquely distinguished by:

1. semi-matte, black to dark purple colored leaves,
2. medium size, rounded lobes and lightly ruffled leaves, 3. small, bi-colored flowers of hot pink and white on medium short spikes,
4. good sun tolerance,
5. a medium, low mounding habit with excellent crown count, and
6. excellent vigor.

This new cultivar has been reproduced only by asexual propagation (tip cuttings and tissue culture using growing tips). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a nine-month-old plant of *Heuchera* 'Dark 'N' Bright' growing in part shade in a one-gallon pot in December in Canby, Oreg.

FIG. 2 shows a ten-month-old plant of *Heuchera* 'Dark 'N' Bright' growing in the trial field in October in Canby, Oreg.

DETAILED PLANT DESCRIPTION

The following is a detailed description of the new *Heuchera* cultivar based on observations taken in September of an eight-month-old specimen growing in a one-gallon pot in partial shade in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5th edition, 2007.

Plant:

*Form.*—Basal rosette, herbaceous perennial.

*Hardiness.*—USDA Zone 4 to 9.

*Size.*—14.5 cm tall from top of the foliage to the ground, 26.5 cm from ground to top of flowers, 34 cm wide.

*Number of crowns.*—About 18.

*Habit.*—Medium, low mound.

*Vigor.*—Excellent.

Leaf:

*Type.*—Simple.

*Arrangement.*—Rosette.

*Shape.*—Widely depressed ovate.

*Number.*—About 65.

*Blade size.*—Grows to 11.5 cm long and 11 cm wide.

*Venation.*—Palmate.

*Lobing/Division.*—Palmately lobed with 5 main lobes with secondary lobes.

*Margins.*—Crenate and undulate.

*Apex.*—Mucronulate.

*Base.*—Cordate.

*Surface texture.*—Glandular-puberulent on both sides.

*Leaf rugosity.*—Weak.

*Leaf undulation.*—Weak.

*Petiole description.*—Grows to 9 cm long and 3 mm wide, glandular hairs, Greyed Purple 187A.

*Leaf color.*—Topside between Black 203A and Greyed Purple 187A including veins, bottom side Greyed Purple187A including veins.

Inflorescence:

*Size.*—Grows to 6 cm wide and 12 cm long.

*Type.*—Upright thyrse.

*Number of flowers per thyrse.*—About 50.

*Flower density.*—Moderate to light.

*Number of thyrse.*—Up to 20.

*Peduncle.*—Grows to 14.5 cm long and 3 mm wide at base, glandular hairs, between Black 203A and Greyed Purple 187A.

*Flowering stem attitude.*—Upwards.

*Pedicel.*—Grows to 3 mm long, with glandular hairs, between Black 203A and Greyed Purple 187A.

*Bloom period.*—July to frost in Canby, Oreg.

Flower bud:

*Size.*—4 mm wide and 5 mm long.

*Description.*—Glandular-puberulent, ovoid, horizontal to down facing.

*Color.*—Red Purple 63A tinted White N155C.

Flower:

*Type.*—Perfect.

*Shape.*—Campanulate.

*Attitude.*—Side-facing.

*Size.*—9 mm long and 5 mm wide.

*Corolla description.*—5 petals, each 2 mm long and 1 mm wide, spatulate, margins entire, tip acute, glabrous on topside, glandular-puberulent on bottom side, both sides White N155C.

*Calyx description.*—Campanulate, 7 mm long and 4 mm wide, with 5 lobes with wide sinuses divided ½ way to the base, each 2 mm wide and 3 mm long, oblong in shape, back side glandular-puberulent with glandular hairs, glabrous inside, tip obtuse, margin entire, outside Red Purple 63A on top 2 mm blending to White N155C in middle for 3 mm, blending to Red Purple 63B on bottom 2 mm, inside White N155C.

*Stamen description.*—5 in number, filaments 2.5 mm long, White NN155C, anthers 0.5 mm long, Yellow Orange 22A, pollen absent.

*Pistil description.*—1, 2-beaked, 5 mm long and 2 mm wide, Red Purple 65C overall, ovary 2 mm long and 2 mm wide, style 3 mm long.

*Fragrance.*—None.

*Lastingness.*—Each thyrse blooms for about 3 weeks on the plant.

Fruit:

*Type.*—Two-beaked ovoid capsule.

*Fertility.*—Moderate.

*Color.*—Greyed Brown 199C.

Seed:

*Shape.*—Linear.

*Size.*—2 mm long.

*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

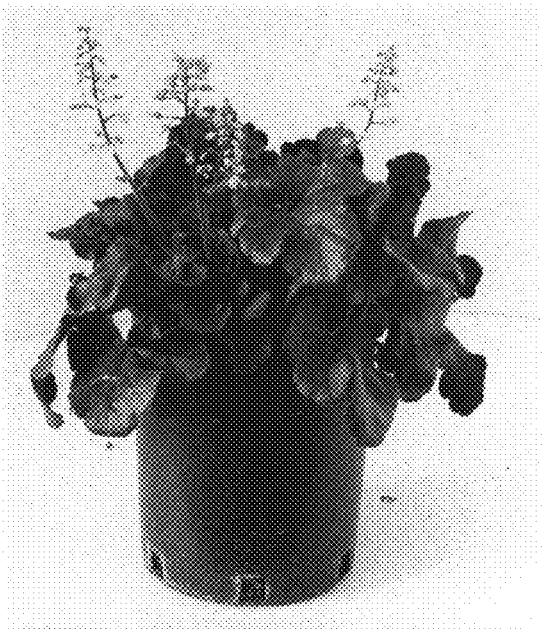
Fig. 1 Left
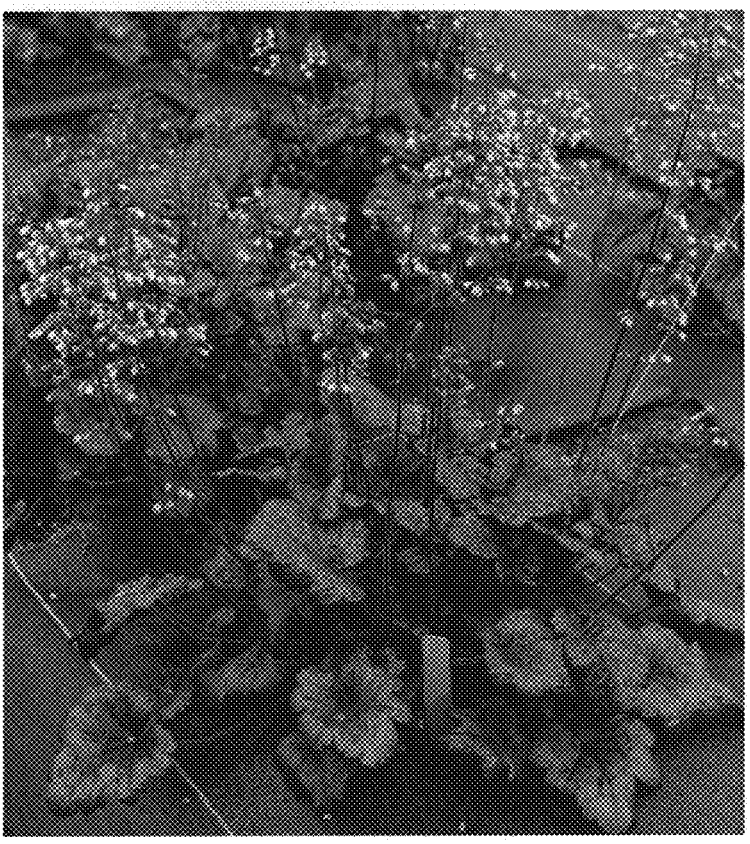
Fig. 2 Left